US009856404B2

(12) United States Patent
Campbell et al.

(10) Patent No.: US 9,856,404 B2
(45) Date of Patent: Jan. 2, 2018

(54) SELF-HEATING SEALANT OR ADHESIVE EMPLOYING MULTI-COMPARTMENT MICROCAPSULES

(71) Applicant: International Business Machines Corporation, Armonk, NY (US)

(72) Inventors: Eric J. Campbell, Rochester, MN (US); Joseph Kuczynski, North Port, FL (US); Kevin A. Splittstoesser, Stewartville, MN (US); Timothy J. Tofil, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 111 days.

(21) Appl. No.: 14/938,044

(22) Filed: Nov. 11, 2015

(65) Prior Publication Data

US 2017/0130102 A1    May 11, 2017

(51) Int. Cl.
| | | |
|---|---|---|
| C08K 9/00 | (2006.01) | |
| C09J 11/04 | (2006.01) | |
| A61K 9/50 | (2006.01) | |
| B01J 13/02 | (2006.01) | |
| B01J 13/22 | (2006.01) | |

(52) U.S. Cl.
CPC ............. *C09J 11/04* (2013.01); *A61K 9/5094* (2013.01); *B01J 13/02* (2013.01); *B01J 13/22* (2013.01)

(58) Field of Classification Search
CPC ... C09J 11/04; B01J 19/087; B01J 2219/0803
See application file for complete search history.

(56) References Cited

U.S. PATENT DOCUMENTS

| | | | |
|---|---|---|---|
| 3,653,372 A | 4/1972 | Douglas | |
| 4,095,583 A | 6/1978 | Petersen et al. | |
| 5,904,796 A * | 5/1999 | Freuler | B32B 7/06 156/278 |
| 5,984,995 A | 11/1999 | White | |
| 6,114,413 A | 9/2000 | Kang et al. | |
| 6,947,285 B2 | 9/2005 | Chen et al. | |
| 7,290,549 B2 | 11/2007 | Banerjee et al. | |
| 7,816,785 B2 | 10/2010 | Iruvanti et al. | |
| 7,834,442 B2 | 11/2010 | Furman et al. | |
| 7,886,813 B2 | 2/2011 | Hua et al. | |
| 8,174,112 B1 | 5/2012 | Karp et al. | |
| 8,741,804 B2 | 6/2014 | Boday et al. | |
| 8,896,110 B2 | 11/2014 | Hu et al. | |
| 2006/0079021 A1 | 4/2006 | Yang | |
| 2006/0228542 A1 | 10/2006 | Czubarow | |
| 2008/0038540 A1* | 2/2008 | Hirayama | C09J 7/0217 428/323 |
| 2013/0034739 A1 | 2/2013 | Boday et al. | |
| 2014/0110049 A1 | 4/2014 | Yuen et al. | |
| 2014/0368992 A1 | 12/2014 | Strader et al. | |
| 2017/0129825 A1* | 5/2017 | Campbell | C06B 47/00 |
| 2017/0130993 A1* | 5/2017 | Campbell | F24J 1/00 |

FOREIGN PATENT DOCUMENTS

| | | |
|---|---|---|
| CA | 918331 | 1/1973 |
| CN | 103740978 A | 4/2014 |
| CN | 103740997 A | 4/2014 |
| JP | 2000317578 A | 11/2000 |
| JP | 2001176924 A | 6/2001 |
| JP | 4073571 B2 | 2/2008 |
| WO | 2009029804 A2 | 3/2009 |
| WO | 2011086018 A1 | 7/2011 |
| WO | 2014204828 A2 | 12/2014 |

OTHER PUBLICATIONS

Yamaura et al., "Preparation and characterization of (3-aminopropyl) triethoxysilane-coated magnetite nanoparticles," Journal of Magnetism and Magnetic Materials, vol. 279, 2004, pp. 210-217.
Kreft et al., "Shell-in-Shell Microcapsules: A Novel Tool for Integrated, Spatially Confined Enzymatic Reactions", Angewandte Chemie International Edition, vol. 46, 2007, pp. 5605-5608.
Xiong et al., "Towards Theranostic Multicompartment Microcapsules: in-situ Diagnostics and Laser-induced Treatment", Theranostics, vol. 3, Issue 3, 2013, pp. 141-151.
Marzzacco, C., "The Effect of a Change in the Catalyst on the Enthalpy of Decomposition of Hydrogen Peroxide," pp. 12-13, Chem 13 News/Nov. 2008, reprinted from pp. 16-17, May 2001.
Masin, G., "The Chemistry of Hand Warmers", 3 pages, printed from <http://www.chemistryislife.com/the-chemistry-of-hand-warmer> on Sep. 14, 2015.
Unknown, "Flameless Chemical Heaters", 2014, zenstoves.net, 4 pages, printed from <http://zenstoves.net/Flameless.htm> on Sep. 14, 2015.
Unknown, "Flameless Ration Heater (FRH)", MREInfo.com, 2014, 5 pages, printed from <http://www.mreinfo.com/us/mre/frh.html> on Sep. 14, 2015.

(Continued)

*Primary Examiner* — Hannah Pak
(74) *Attorney, Agent, or Firm* — Matthew J. Bussan

(57) ABSTRACT

A self-heating sealant or adhesive may be formed using multi-compartment microcapsules dispersed within a sealant or adhesive. The multi-compartment microcapsules produce heat when subjected to a stimulus (e.g., a compressive force, a magnetic field, or combinations thereof). In some embodiments, the multi-compartment microcapsules have first and second compartments separated by an isolating structure adapted to rupture in response to the stimulus, wherein the first and second compartments contain reactants that come in contact and react to produce heat when the isolating structure ruptures. In some embodiments, the multi-compartment microcapsules are shell-in-shell microcapsules each having an inner shell contained within an outer shell, wherein the inner shell defines the isolating structure and the outer shell does not allow the heat-generating chemistry to escape the microcapsule upon rupture of the inner shell.

11 Claims, 8 Drawing Sheets

(56) References Cited

OTHER PUBLICATIONS

Kawashita et al., "In vitro heat generation by ferrimagnetic maghemite microspheres for hyperthermic treatment of cancer under alternating magnetic field.", Journal of Materials Science: Materials in Medicine, vol. 19, Issue 5, 2008, 1897-1903 (Abstract Only, 2 pages), printed from <http://www.ncbi.nlm.nih.gov/pubmed/17914614> on Sep. 14, 2015.
Unknown, "PTFE Coatings," Specific Heat of Some Common Substances, http://www.engineeringtoolbox.com/specific-heat-capacity-d_391.html, printed Jun. 23, 2015. 11:08 AM, 7 pgs.
Unknown, "Standard enthalpy change of formation (data table)", Wikipedia, the free encyclopedia, 2015, 12 pages, printed from <https://en.wikipedia.org/wiki/Standard_enthalpy_change_of_formation_%28data_table%29> on Sep. 14, 2015.
Unknown, "Technical Overview: Microencapsulation", microtek laboratories, inc., 4 pages, downloaded from <http://www.microteklabs.com/technical_overview.pdf> on Sep. 14, 2015.
Unknown, "Thermochemistry", 7 pages, downloaded from <http://smd.gytool.cz/downloads/thermochemistry_bar.pdf> on Sep. 14, 2015.
Delcea et al., "Multicompartmental Micro- and Nanocapsules: Hierarchy and Applications in Biosciences", Macromolecular Bioscience, vol. 10, 2010, pp. 465-474.
Lee, J.H., "Microencapsulated Heat Generating Material to Accelerate the Curing Process During Liquid Crystal Display Fabrication", NineSigma, Inc., 2014, 3 pages, printed from <https://ninesights.ninesigma.com/rips/-/rfp-portlet/rfpViewer/2690> on Sep. 22, 2015.
Brown et al., "In situ poly(urea-formaldehyde) microencapsulation of dicyclopentadiene", Journal of Microencapsulation, vol. 20, No. 6, 2003, pp. 719-730.
Keller et al., "Mechanical Properties of Microcapsules Used in a Self-Healing Polymer", Experimental Mechanics, vol. 46, 2006, pp. 725-733.
Hu et al., "Controlled Rupture of Magnetic Polyelectrolyte Microcapsules for Drug Delivery", Langmuir, vol. 24, 2008, pp. 11811-11818.
Unknown, "Materials for Sealing Liquid Crystal", Three Bond Technical News, Three Bond Co., Ltd., vol. 43, 1994, pp. 1-8.
Unknown, "Advanced Technologies for LCD Assembly", Dow Corning Corporation, 2014, 4 pages, downloaded from <http://www.dowcoming.com/content/publishedlit/11-3437_Advanced_Technologies_LCD_Assembly.pdf?wt.svl=ELEC_LHH> on Oct. 23, 2015.
Unknown, "Loctite Eccobond DS 6601", Henkel Corporation, 2013, 2 pages, downloaded from <https://tds.us.henkel.com/NA/UT/HNAUTTDS.nsf/web/C0DD8377AB27D63985257B41005DC4A1/$File/LOCTITE%20ECCOBOND%20DS%206601-EN.pdf> on Oct. 27, 2015.
Stober et al., "Controlled Growth of Monodisperse Silica Spheres in the Micron Size Range," Journal of Colloid and Interface Science 26, pp. 62-69 (1968).
U.S. Appl. No. 14/937,944, to Eric J. Campbell et al., entitled "Self-Heating Thermal Interface Material", filed Nov. 11, 2015, assigned to International Business Machines Corporation.
U.S. Appl. No. 14/937,983, to Eric J. Campbell et al., entitled "Heat-Generating Multi-Compartment Microcapsules", filed Nov. 11, 2015, assigned to International Business Machines Corporation.
List of IBM Patents or Patent Applications Treated as Related.
U.S. Appl. No. 15/717,740, to Eric J. Campbell et al., entitled "Self-Heating Sealant or Adhesive Employing Multi-Compartment Microcapsules", filed Sep. 27, 2017, assigned to International Business Machines Corporation.
List of IBM Patents or Patent Applications Treated as Related (Updated Sep. 28, 2017).
U.S. Appl. No. 15/808,995, to Eric J. Campbell et al., entitled "Self-Heating Sealant or Adhesive Employing Multi-Compartment Microcapsules", filed Nov. 10, 2017, assigned to International Business Machines Corporation.
List of IBM Patents or Patent Applications Treated as Related (Updated Nov. 11, 2017).

* cited by examiner

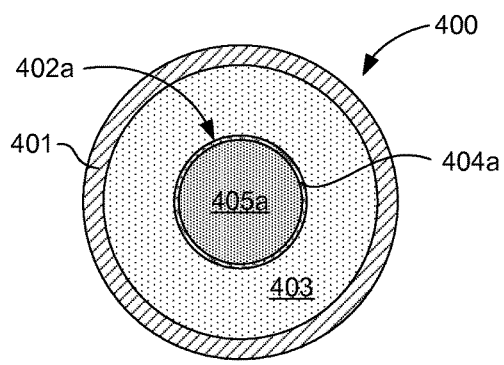 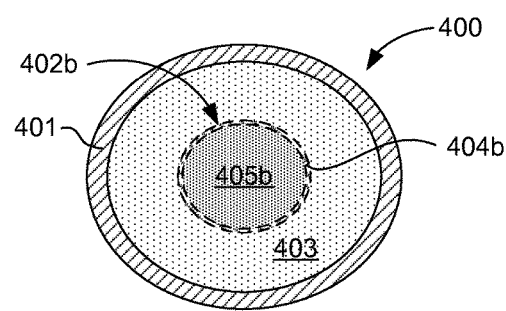
FIG. 4A  FIG. 4B
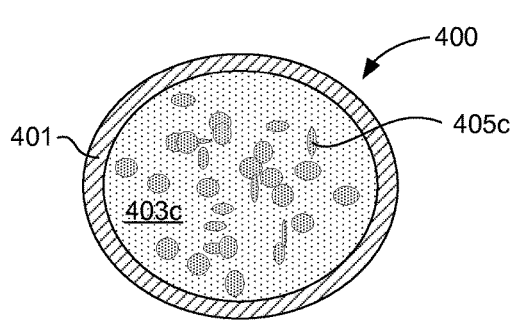 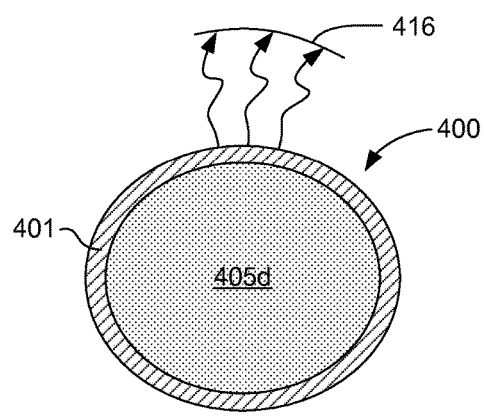
FIG. 4C  FIG. 4D

SELF-HEATING SEALANT OR ADHESIVE EMPLOYING MULTI-COMPARTMENT MICROCAPSULES

BACKGROUND

The present invention relates in general to the field of materials science. More particularly, the present invention relates to self-heating sealants or adhesives employing multi-compartment microcapsules for heat generation to enhance curing.

SUMMARY

A self-heating sealant or adhesive includes multi-compartment microcapsules that increase the temperature of the sealant or adhesive during curing, e.g., during the process of assembling liquid crystal cells when a sealant is used to seal the periphery of a liquid crystal layer between a thin-film transistor (TFT) array substrate and a color filter substrate. Aspects of the present invention describe a method of producing a self-heating sealant or adhesive, a self-heating sealant or adhesive, and a method of curing a heat-sourcing sealant or adhesive.

According to some embodiments of the present invention, a self-heating sealant or adhesive is prepared by dispersing multi-compartment microcapsules within a sealant or adhesive. The multi-compartment microcapsules produce heat when subjected to a stimulus (e.g., a compressive force, a magnetic field, ultrasound, or combinations thereof). In some embodiments, the multi-compartment microcapsules have first and second compartments separated by an isolating structure adapted to rupture in response to the stimulus, wherein the first and second compartments contain reactants that come in contact and react to produce heat when the isolating structure ruptures. In some embodiments, the multi-compartment microcapsules are shell-in-shell microcapsules each having an inner shell contained within an outer shell, wherein the inner shell defines the isolating structure and the outer shell does not allow the heat-generating chemistry to escape the microcapsule upon rupture of the inner shell.

BRIEF DESCRIPTION OF THE SEVERAL VIEWS OF THE DRAWINGS

Embodiments of the present invention will hereinafter be described in conjunction with the appended drawings, where like designations denote like elements.

FIG. 4A illustrates a multi-compartment microcapsule containing reactants according to some embodiments of the present disclosure.

FIG. 4B illustrates a multi-compartment microcapsule in which the capsule wall of the inner microcapsule is ruptured according to some embodiments of the present disclosure.

FIG. 4C illustrates a multi-compartment microcapsule in which a first reactant is dispersed within a second reactant according to some embodiments of the present disclosure.

FIG. 4D illustrates a multi-compartment microcapsule in which the reactants within the microcapsule have generated heat according to some embodiments of the present disclosure.

DETAILED DESCRIPTION

Figure 1:
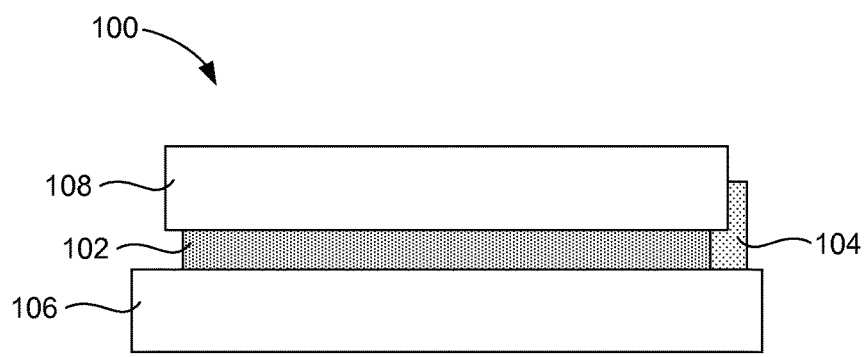
FIG. 1 illustrates a stage of TFT LCD panel fabrication (i.e., during a process of assembling liquid crystal cells) in which a self-heating sealant is used to seal the periphery of a liquid crystal layer between a TFT array substrate and a color filter substrate according to some embodiments of the present disclosure.

Aspects of the present disclosure relate to a self-heating sealant or adhesive having multi-compartment microcapsules dispersed within a sealant or adhesive. Other aspects of the present disclosure relate to a method of producing a self-heating sealant or adhesive having multi-compartment microcapsules dispersed within a sealant or adhesive. Still other aspects of the present disclosure relate to a method of curing a self-heating sealant or adhesive having multi-compartment microcapsules dispersed within the sealant or adhesive. Yet other aspects of the present disclosure relate to forming and activating multi-compartment microcapsules for heat generation in sealants, adhesives, or other materials that would benefit from their inclusion such as thermal interface materials (TIMs), coatings, paints, varnishes, encapsulants, and the like.

Benefits that may be achieved by inclusion of multi-compartment microcapsules for heat generation in materials such as sealants, adhesives, TIMs, coatings, paints, varnishes, encapsulants, and the like, include, but are not limited to, reduced cure time, reduced viscosity, and increased compliance. Compliance is a measure of the ability of a material to flow. Materials with a lower compliance produce thicker bond lines. Heating a material through activation of multi-component microcapsules including the material for heat generation may increase its compliance and correspondingly produce a thinner bond line.

A self-heating sealant or adhesive, in accordance with some embodiments of the present disclosure, comprises multi-compartment microcapsules dispersed within a sealant or adhesive. The multi-compartment microcapsules produce heat when subjected to a stimulus (e.g., a compressive force, a magnetic field, ultrasound, or combinations thereof). In some embodiments, the multi-compartment microcapsules have first and second compartments separated by an isolating structure adapted to rupture in response to the stimulus, wherein the first and second compartments contain reactants that come in contact and react to produce heat when the isolating structure ruptures. In some embodiments, the multi-compartment microcapsules are shell-in-shell microcapsules each having an inner shell contained within an outer shell, wherein the inner shell defines the isolating structure and the outer shell does not allow the heat-generating chemistry to escape the microcapsule upon rupture of the inner shell.

Sealants and adhesives are often pigeon-holed together, but these terms are not always interchangeable. An adhesive is designed to bond two or more items together. A sealant is designed to fill a gap between two or more items to prevent contaminants (e.g., moisture and gases) from infiltrating therebetween. An adhesive is not necessarily a sealant, and visa-versa.

Multi-compartment microcapsules are known in the art to be formed in a variety of structural configurations (e.g., concentric, pericentric, innercentric, or acentric). Multi-compartment microcapsules include at least two compartments that are separated from each other. The compartments within a multi-compartment microcapsule may contain various chemical elements or compounds. Multi-compartment microcapsules may be produced using techniques well known to those skilled in the art.

In the embodiments that follow, exemplary self-heating sealants and exemplary self-heating adhesives are employed in the context of thin-film transistor (TFT) liquid crystal display (LCD) panel fabrication. These exemplary self-heating sealants and adhesives are set forth for purposes of illustration, not limitation. One skilled in the art will appreciate that a self-heating sealant or adhesive consistent with the spirit of the present disclosure may be used in other contexts.

Sealants and adhesives are used in many stages of TFT LCD panel fabrication, including the liquid crystal cell assembly process and the LCD module assembly process.

For example, during the process of assembling liquid crystal cells (i.e., also referred to as the liquid crystal cell assembly process), a sealant is used to seal the periphery of a liquid crystal layer between a TFT array substrate and a color filter substrate. The substrates are brought together with the sealant interposed therebetween at the periphery of the substrates while a cell gap between the substrates is maintained by spacers. Two main types of conventional sealants are used during this stage of LCD manufacturing: thermally-cured sealants (e.g., epoxy resin) and UV-cured sealants (e.g., acrylic resin). These conventional sealants are typically applied by screen-printing or through the use of sealant dispensers (e.g., one or more dispensing heads). Unfortunately, these conventional sealants typically impede speeding up production and achieving higher unit-volume throughput because they require the use of heat ovens and/or ultraviolet lamps.

FIG. 1 illustrates a stage of TFT LCD panel fabrication (i.e., during a process of assembling a liquid crystal cell 100) in which a self-heating sealant (e.g., an LCD panel main sealant 102 and/or an LCD panel end sealant 104) is used to seal the periphery of a liquid crystal layer (not shown in FIG. 1) between a TFT array substrate 106 and a color filter substrate 108 according to some embodiments of the present disclosure. In accordance with some embodiments of the present disclosure, the LCD panel main sealant 102 may be a self-heating sealant having multi-compartment microcapsules dispersed in a resin (epoxy) based sealant, such as UV- and heat-curable epoxy resins. The multi-compartment microcapsules contained in the LCD panel main sealant 102 may be activated, for example, by a compressive force applied via pressure bonding when the substrates 106, 108 are brought together with the LCD panel main sealant 102 interposed therebetween. Similarly, in accordance with some embodiments of the present disclosure, the LCD panel end sealant 104 may be a self-heating sealant having multi-compartment microcapsules dispersed in a resin (epoxy) based sealant, such as UV- and heat-curable epoxy resins. The multi-compartment microcapsules contained in the LCD panel end sealant 104 may be activated, for example, by a compressive force applied by a sealant dispenser (e.g., a dispensing head used to dispense the LCD panel end sealant 104). An exemplary process of assembling a liquid crystal cell during TFT LCD panel fabrication, in which a self-heating sealant is used in accordance with some embodiments of the present disclosure, is described below with reference to FIG. 9.

Figure 2:
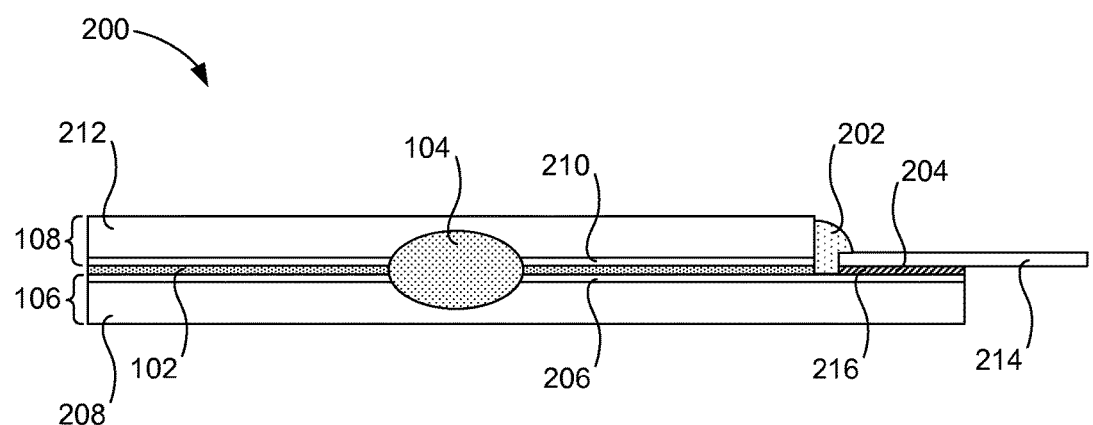
FIG. 2 illustrates a stage of TFT LCD panel fabrication (i.e., during a process of assembling LCD modules) in which a self-heating sealant is used as a terminal sealant according to some embodiments of the present disclosure.

FIG. 2 illustrates a stage of TFT LCD panel fabrication (i.e., during a process of assembling LCD module 200) in which a self-heating sealant (e.g., a terminal sealant 202) is used to seal the transparent display/backlight electrodes of the LCD module 200 and a self-heating adhesive (e.g., an anisotropically conductive adhesive 204) is used to form mechanical bonding and electrical connections between the transparent display/backlight electrodes of the LCD module 200 and a driver flexible printed circuit (FPC) 214 according to some embodiments of the present disclosure.

A transparent, electrically conductive indium tin oxide (ITO) layer 206, which provides transparent display/backlight panel electrodes of the LCD module 200, is sputter deposited on a glass substrate 208 of the TFT array substrate 106. Similarly, an ITO layer 210 is sputter deposited on the glass substrate 212 of the color filter substrate 108. The anisotropically conductive adhesive 204, which is used to form mechanical bonding and electrical connections between the transparent display/backlight electrodes and a driver FPC 214, cures to provide an anisotropically conductive film (ACF) 216. In accordance with some embodiments of the present disclosure, the anisotropically conductive adhesive 204 may be a self-heating adhesive having multi-compartment microcapsules dispersed in an anisotropically conductive adhesive, such as ThreeBond 3370G. Anisotropically conductive adhesives (which are also referred to as "anisotropically conductive pastes") are typically made of thermoplastic resin in which a conductive filler is dispersed. The multi-compartment microcapsules contained in the anisotropically conductive adhesive 204 may be activated, for example, by a compressive force applied via pressure bonding when the ITO layer 206/glass substrate 208 and the driver FPC 214 are brought together with the anisotropically conductive adhesive 204 interposed therebetween.

The terminal sealant 202, which seals the display/backlight electrodes of the LCD module 200, preferably has strong adhesion to the glass substrates 208, 212, the ITO layers 210, 206, the driver FPC 214, and the ACF 216. In accordance with some embodiments of the present disclosure, the terminal sealant 202 may be a self-heating sealant having multi-compartment microcapsules dispersed in a silicone sealant, such as Dow Corning SE9187 L or Dow Corning EA-3000. The multi-compartment microcapsules contained in the terminal sealant 202 may be activated, for example, by a compressive force applied by a sealant dispenser (e.g., a dispensing head used to dispense the terminal sealant 202).

Figure 3A:
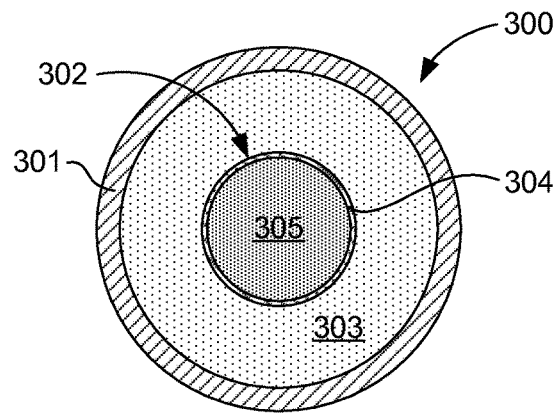
FIG. 3A depicts a multi-compartment microcapsule having a shell-in-shell architecture with an inner shell contained within an outer shell, wherein the inner shell is adapted to rupture in response to a compressive force according to some embodiments of the present disclosure.

FIG. 3A depicts a multi-compartment microcapsule 300 having a shell-in-shell architecture with an inner shell contained within an outer shell, wherein the inner shell is adapted to rupture in response to a compressive force according to some embodiments of the present disclosure. In FIG. 3A, the multi-compartment microcapsule 300 is illustrated in a cutaway view. The multi-compartment microcapsule 300 has an outer wall 301 (also referred to herein as the "outer shell" 301 of the multi-compartment microcapsule 300) and contains an inner microcapsule 302 and a first reactant 303. The inner microcapsule 302 has a capsule wall 304 (also referred to herein as the "inner shell" 304 of the multi-compartment microcapsule 300) and contains a second reactant 305. The first reactant 303 within the multi-compartment microcapsule 300 may surround the inner microcapsule 302, and the first reactant 303 may be prevented from contacting the second reactant 305 by the capsule wall 304 of the inner microcapsule 302.

The capsule wall 304 of the inner microcapsule 302 may be formed to rupture under a particular compressive force and the outer wall 301 of the microcapsule 300 may be formed so as to not rupture under that compressive force. Rupturing the capsule wall 304 of the inner microcapsule 302 may allow the second reactant 305 to contact the first reactant 303 and the reactants may then chemically or physically react. In various embodiments, the reaction may be exothermic.

Figure 3B:
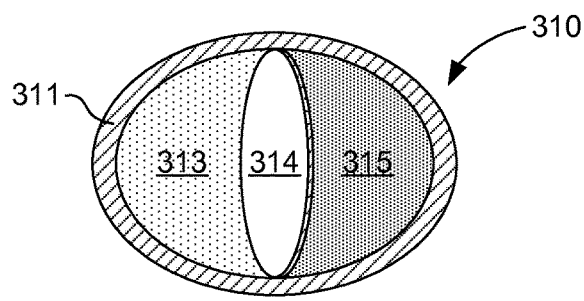
FIG. 3B depicts a multi-compartment microcapsule having an inner barrier to form compartments, wherein the inner barrier is adapted to rupture in response to a compressive force according to some embodiments of the present disclosure.

FIG. 3B depicts a multi-compartment microcapsule 310 having an inner barrier to form compartments, wherein the inner barrier is adapted to rupture in response to a compressive force according to some embodiments of the present disclosure. In FIG. 3A, the multi-compartment microcapsule 310 is illustrated in a cutaway view. The multi-compartment microcapsule 310 has an outer wall 311 and contains a first reactant 313 and a second reactant 315. A membrane 314 within the multi-compartment microcapsule 310 may prevent the first reactant 313 and the second reactant 315 from coming into contact. The membrane 314 may be any form of a physical barrier that forms two or more compartments within the microcapsule 310.

The membrane 314 may be formed to rupture under a particular compressive force and the outer wall 311 of the multi-compartment microcapsule 310 may be formed so as to not rupture under that compressive force. Rupturing the membrane 314 may allow the first reactant 313 to contact the second reactant 315 and the reactants may then chemically or physically react. In various embodiments, the reaction may be exothermic.

In accordance with some embodiments, the compressive force applied to a self-heating sealant or adhesive may be within the range typical of that applied in the manufacture or repair of electronic assemblies (e.g., during the process of assembling liquid crystal cells, during the process of assembling LCD modules, and the like). In accordance with some embodiments, the inner capsule wall 304 (of the multi-compartment microcapsule 300 shown in FIG. 3A), or a membrane 314 (of the multi-compartment microcapsule 310 shown in FIG. 3B), may rupture at a force no greater than the lower bound of this range of compressive force. The outer wall 301 (of the multi-compartment microcapsule 300 shown in FIG. 3A), or the outer wall 311 (of the multi-compartment microcapsule 310 shown in FIG. 3B), may sustain, without rupturing, a force no less than the upper bound of this range of compressive force.

Other embodiments may utilize more than two reactants. The multi-compartment microcapsule 300 of FIG. 3A may contain a plurality of inner microcapsules, such as 302, and the inner microcapsules may themselves contain other, inner, microcapsules. The various microcapsules may contain reactants and may rupture under compression to allow the reactants to come into contact. Similarly, the multi-compartment microcapsule 310 of FIG. 3B may contain a plurality of compartments formed by a plurality of membranes or barriers, such as 314, and the compartments may in turn contain one or more membranes or barriers, or may contain microcapsules. The various membranes or barriers may rupture under compression to allow the reactants to come into contact.

Figure 3C:
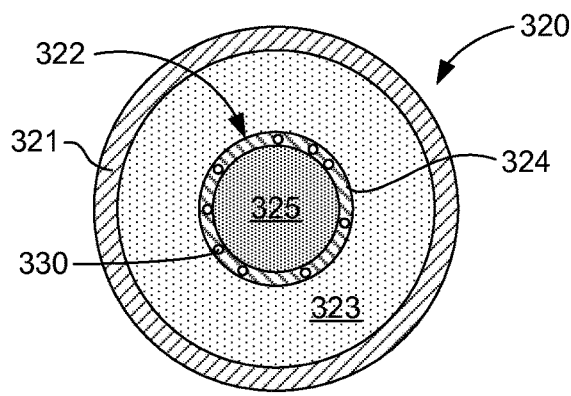
FIG. 3C depicts a multi-compartment microcapsule having a shell-in-shell architecture with an inner shell contained within an outer shell, wherein the inner shell is adapted to rupture in a magnetic field according to some embodiments of the present disclosure.

FIG. 3C depicts a multi-compartment microcapsule 320 having a shell-in-shell architecture with an inner shell contained within an outer shell, wherein the inner shell is adapted to rupture in a magnetic field according to some embodiments of the present disclosure. In FIG. 3C, the multi-compartment microcapsule 320 is illustrated in a cutaway view. The multi-compartment microcapsule 320 depicted in FIG. 3C is similar to the multi-compartment microcapsule 300 depicted in FIG. 3A, but one or more magnetic nanoparticles 330 are incorporated into the inner shell of the multi-compartment microcapsule 320. The multi-compartment microcapsule 320 has an outer wall 321 (also referred to herein as the "outer shell" 321 of the multi-compartment microcapsule 320) and contains an inner microcapsule 322 and a first reactant 323. The inner microcapsule 322 has a capsule wall 324 (also referred to herein as the "inner shell" 324 of the multi-compartment microcapsule 320) and contains a second reactant 325. The first reactant 323 within the multi-compartment microcapsule 320 may surround the inner microcapsule 322, and the first reactant 323 may be prevented from contacting the second reactant 325 by the capsule wall 324 of the inner microcapsule 322.

With regard to the multi-compartment microcapsule 320 depicted in FIG. 3C, in accordance with some embodiments of the present disclosure, a magnetic field generating device generates a magnetic field sufficient to rupture the "inner shell" 324 of the multi-compartment microcapsules 320 dispersed in a sealant or adhesive through magnetic stimulation of the magnetic nanoparticles 330. Application of a sufficiently strong high-frequency magnetic field causes the magnetic nanoparticles 330 embedded in the "inner shell" 324 of the multi-compartment microcapsules 320 to rotate and/or vibrate at an accelerated rate thereby rupturing the "inner shell" 324 and, in turn, permit the first reactant 323 and the second reactant 325 to contact one another, react, and generate heat. Preferably, the high-frequency magnetic field applied to the self-heating sealant or adhesive by the magnetic field generating device has a frequency of approximately 50-100 kHz and a strength of approximately 2.5 kA/m or 31 Oe.

The capsule wall 324 of the inner microcapsule 322 may be formed with one or more magnetic nanoparticles 330 to rupture under a particular magnetic field through magnetic stimulation of the one or more magnetic nanoparticles 330 and the outer wall 321 of the microcapsule 320 may be formed so as to not rupture under that magnetic field. Rupturing the capsule wall 324 of the inner microcapsule 322 may allow the second reactant 325 to contact the first reactant 323 and the reactants may then chemically or physically react. In various embodiments, the reaction may be exothermic.

FIG. 4A, FIG. 4B, FIG. 4C, and FIG. 4D illustrate configurations of a microcapsule under a compressive force, and the compression causing the reactants within the microcapsule to mix, according to some embodiments of the present disclosure. FIG. 4A illustrates a first microcapsule containing reactants and an inner microcapsule. FIG. 4B illustrates the first microcapsule of FIG. 4A in which the inner microcapsule wall is ruptured. FIG. 4C illustrates the first microcapsule of FIG. 4B in which a reactant contained in the inner microcapsule is dispersed within a reactant initially surrounding the inner microcapsule. FIG. 4D illustrates the first microcapsule of FIG. 4C in which the reactants have produced a reaction product within the first microcapsule and generated heat.

In more detail, FIG. 4A illustrates a microcapsule 400 formed to have a structure similar to that of the multi-compartment microcapsule 300 of FIG. 3A. Microcapsule 400 may have an outer wall 401 and may contain a first reactant 403 and an inner capsule 402a. The inner capsule 402a may have an outer capsule wall 404a and may contain a second reactant 405a.

A compressive force may be applied to the multi-compartment microcapsule 400, which may cause the capsule wall 404a of an inner microcapsule 402a to rupture. FIG. 4B illustrates a second configuration of microcapsule 400 in which the capsule wall 404b of the inner microcapsule 402b may rupture under compression of the microcapsule 400, indicated by the broken line of the capsule wall 404b. FIG. 4C illustrates a third configuration of microcapsule 400 in which the second reactant 405c may become dispersed within the first reactant 403c, in response to the inner microcapsule 402b having ruptured. The dispersion of the second reactant 405c within the first reactant 403c may cause them to react.

FIG. 4D illustrates a fourth configuration of microcapsule 400 in which the reactants 403c and 405c may have come into contact and may have reacted. The fourth configuration of the microcapsule 400 may contain the product 405d of the reaction of 403c and 405c and the outer wall 401 may contain the reaction product 405d so as to prevent the reaction product from contacting a material in which microcapsule 400 may be itself dispersed. The reactants 403c and 405c may have reacted exothermically to produce heat 416, and the heat may, as illustrated in FIG. 4D, transfer from the microcapsule 400 to a material in which the microcapsule is dispersed.

In accordance with some embodiments of the present disclosure, a self-heating sealant or adhesive may utilize a multi-compartment microcapsule containing an oxidizing and a reducing agent to produce an exothermic reaction, such as oxygen and iron, respectively, according to the reaction equation:

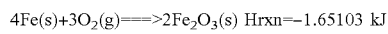

$$4Fe(s)+3O_2(g) \Longrightarrow 2Fe_2O_3(s) \quad Hrxn=-1.65103 \text{ kJ}$$

According to the reaction equation, 4 moles of iron react with 3 moles of oxygen, such that in an embodiment iron may comprise 53% of the combined mass of the two reactants and oxygen may comprise 43% of that combined mass. In an additional embodiment, a multi-compartment microcapsule may contain iron powder and hydrogen peroxide. The iron powder may be mixed with a catalyst such as ferric nitrate, which when in contact with the hydrogen peroxide liberates oxygen to react exothermically with the iron powder. For example, the multi-compartment microcapsule may use 1.5 moles of hydrogen peroxide per mole of iron, for example 0.56 grams of iron powder to 0.51 grams of hydrogen peroxide. The catalytic amount of ferric nitrate may be chosen to achieve a desired reaction rate of heating, in Kilojoules per second. For example, between 0.001 and 0.005 gram equivalents of ferric nitrate per liter of hydrogen peroxide results in a reaction rate producing heat at between 100 and 500 Kilojoules per second.

With reference again to the multi-compartment microcapsule 300 of FIG. 3A, a multi-compartment microcapsule may contain a mixture of iron powder and ferric nitrate in the inner microcapsule 302 as the second reactant 305 and may contain hydrogen peroxide as the first reactant 303 surrounding the inner microcapsule 302. Alternatively, a multi-compartment microcapsule may contain hydrogen peroxide in the inner microcapsule 302 as the second reactant 305 and may contain a mixture of iron powder and ferric nitrate as the first reactant 303 surrounding the inner microcapsule 302. In some embodiments, a multi-compartment microcapsule may have a diameter of less than 5.0 microns, or a multi-compartment microcapsule may have a smaller diameter of less than 2.0 microns. A ratio of 0.2 percent of such multi-compartment microcapsules per unit mass of the sealant or adhesive may produce a temperature increase of at least 1.04 degrees C. per gram of sealant or adhesive.

A structure similar to multi-compartment microcapsule 310 of FIG. 3B, including the various embodiments thereof, may operate similarly to the microcapsule 400 of FIG. 4A through FIG. 4D to rupture the membrane 314, mix the reactants 313 and 315, and produce heat from an exothermic reaction 416 of the reactants. It would be further apparent to one of ordinary skill in that art that an exothermic reaction may be produced by more than two reactants, and that more than two reactants within a capsule may be isolated by more than one inner capsule or membrane, or more than one of any other form of barrier isolating the reactants within the capsule. A variety of reactants may be substituted to produce an exothermic reaction, or a variety of reaction rates and total heat produced, in accordance with some embodiments of the present disclosure.

Figure 5:
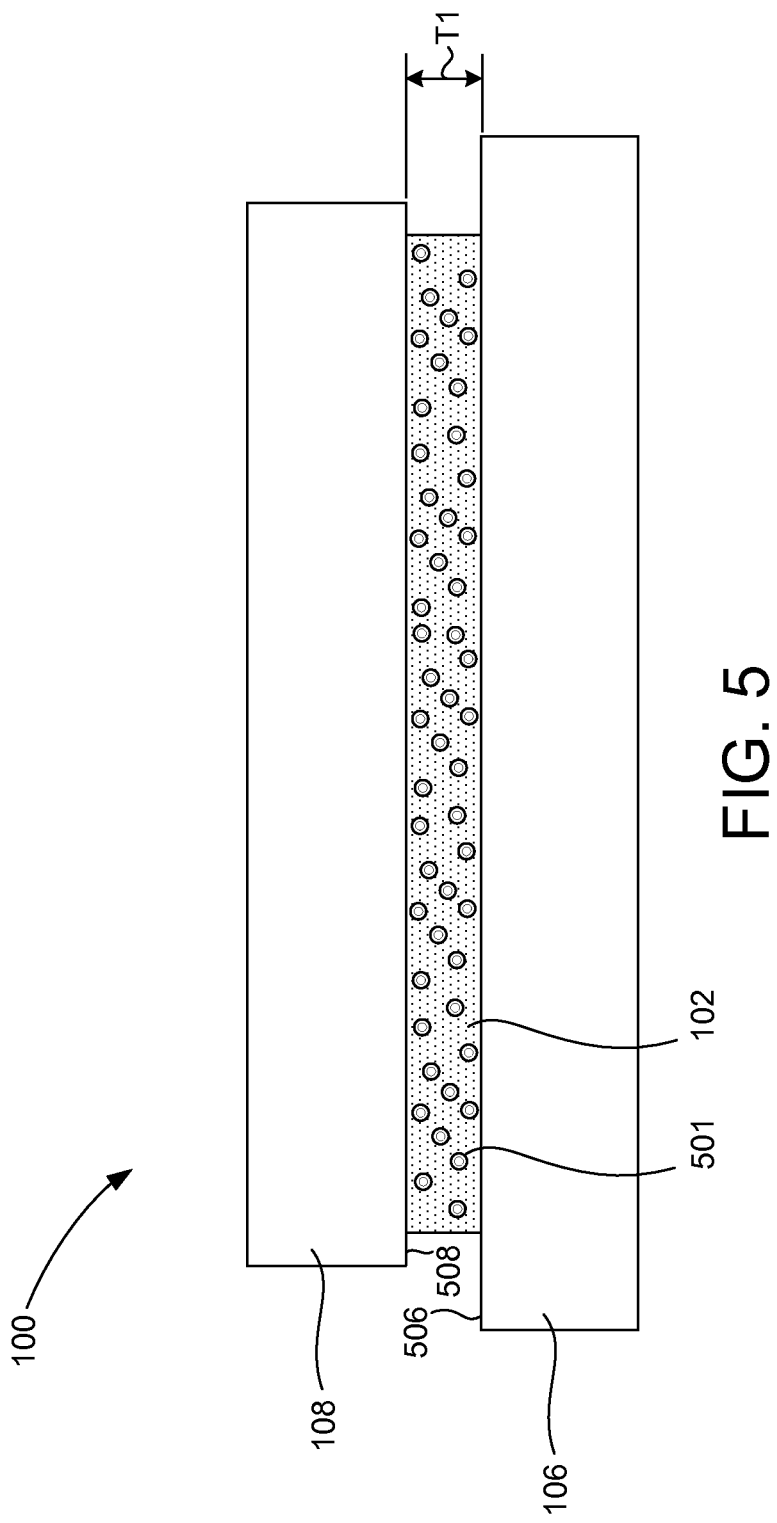
FIG. 5 is an enlarged cutaway view of the liquid crystal cell shown in FIG. 1 in an earlier stage of TFT LCD panel fabrication (i.e., during the LCD module assembly process, but before the LCD panel end-seal sealant is applied), depicting LCD panel main sealant as a self-heating sealant interspersed with multi-compartment microcapsules for heat generation according to some embodiments of the present disclosure.

FIG. 5 is an enlarged cutaway view of the liquid crystal cell 100 shown in FIG. 1 in an earlier stage of TFT LCD panel fabrication (i.e., during the LCD module assembly process, but before the LCD panel end-seal sealant 104 shown in FIG. 1 is applied), depicting the LCD panel main sealant 102 as a self-heating sealant interspersed with multi-compartment microcapsules 501 for heat generation according to some embodiments of the present disclosure. The LCD panel main sealant 102 contacts the TFT array substrate 106 at surface 506 and the color filter substrate 108 at surface 508, and may have a bond line (i.e., the mass of the sealant 102 between surfaces 506 and 508) thickness T1 at ambient temperatures. The LCD panel main sealant 102 may have dispersed within it a plurality of multi-compartment microcapsules 501 for generating heat in response to a stimulus, such as a compressive force, a magnetic field, and the like.

For example, in accordance with some embodiments of the present disclosure, when the LCD panel main sealant 102 is compressed between the TFT array substrate 106 and the color filter substrate 108, the multi-compartment microcapsules 501 may initiate a reaction and the reaction may produce heat. Alternatively, in accordance with other embodiments of the present disclosure, when the LCD panel main sealant 102 interposed between the TFT array substrate 106 and the color filter substrate 108 and subjected to a magnetic field, the multi-compartment microcapsules 501 may initiate a reaction and the reaction may produce heat. The heat may be transferred to the LCD panel main sealant 102, and heating the LCD panel main sealant 102 may cure the LCD panel main sealant 102. In addition, heating the LCD panel main sealant 102 may increase the compliance of the LCD panel main sealant 102. Increasing the compliance of the LCD panel main sealant 102 may produce a bond line thickness of the LCD panel main sealant 102 less than T1. In the various embodiments, the multi-compartment microcapsules 501 may be a structure similar to the multi-compartment microcapsule 300 or 310 as described in reference to FIG. 3A and FIG. 3B, respectively, or may be a structure similar to the multi-compartment microcapsule 320 as described in reference to FIG. 3C. Some embodiments of the present disclosure may disperse multi-compartment microcapsules 501, such as microcapsules 300, 310, or 320, in an LCD panel main sealant 102, and an LCD panel main sealant 102 may be an epoxy-based sealant, an acrylic-based sealant, a silicone-based sealant, and combinations thereof.

Figure 6:
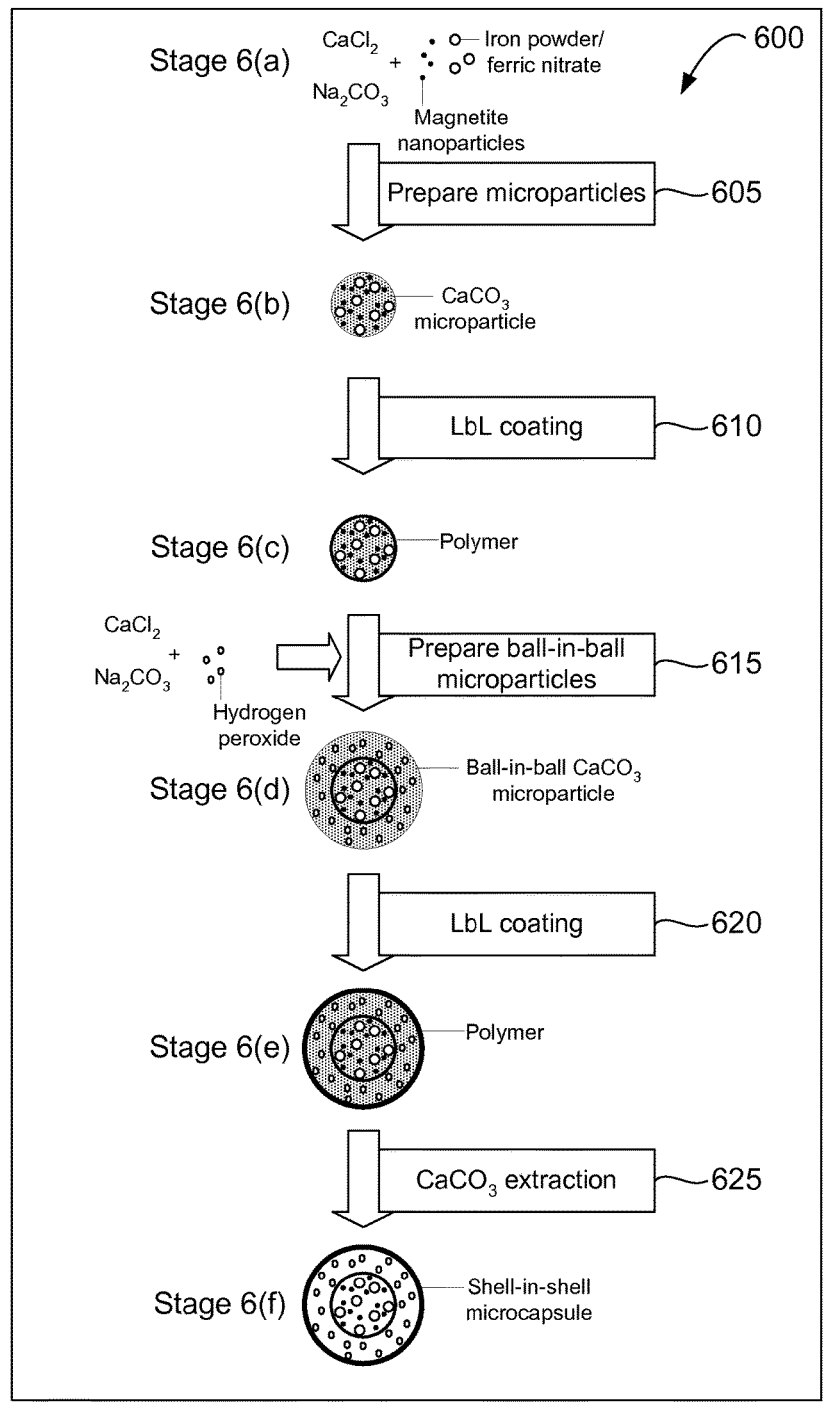
FIG. 6 is a flow diagram illustrating, through stages 6(a)-6(f), a method of producing a multi-compartment microcapsule having a shell-in-shell architecture with an inner shell contained within an outer shell, wherein the inner shell is adapted to rupture in response to a compressive force and/or a magnetic field according to some embodiments of the present disclosure.

FIG. 6 is a flow diagram illustrating, through stages 6(*a*)-6(*f*), a method 600 of producing a multi-compartment microcapsule having a shell-in-shell architecture with an inner shell contained within an outer shell, wherein the inner shell is adapted to rupture in response to a compressive force and/or a magnetic field according to some embodiments of the present disclosure. In the method 600, the steps discussed below (steps 605-625) are performed. These steps are set for the in their preferred order. It must be understood, however, that the various steps may occur simultaneously or at other times relative to one another. Moreover, those skilled in the art will appreciate that one or more steps may be omitted.

In method 600, magnetic nanoparticles are used in step 605 for incorporation into the "inner core" $CaCO_3$ microparticles (shown at stage 6(*b*)) and, optionally, in step 610 for incorporation into the "inner shell" polyelectrolyte multilayer (i.e., the "Polymer" shown at stage 6(*c*)). Magnetic nanoparticles are incorporated into the "inner core" $CaCO_3$ microparticles for the purpose of subsequently magnetically isolating the product prepared in step 615 (i.e., ball-in-ball $CaCO_3$ microparticles) from a coproduct (i.e., single core $CaCO_3$ microparticles). Magnetic nanoparticles are optionally incorporated into the "inner shell" polyelectrolyte multilayer for the purpose of adapting the inner shell of the shell-in-shell microcapsule to rupture in response to a magnetic field. The shell-in-shell microcapsule that results from this optional incorporation of magnetic nanoparticles into the inner shell corresponds to the multi-compartment microcapsule shown in FIG. 3C.

The magnetic nanoparticles may be, for example, $Fe_3O_4$ (also referred to as "magnetite") nanoparticles, cobalt ferrite nanoparticles, or other magnetic nanoparticles known in the art. Preferably, the magnetic nanoparticles have a diameter in the range of approximately 6-25 nm.

The magnetic nanoparticles are prepared using conventional techniques known to those skilled in the art. For example, magnetite nanoparticles may be prepared using a conventional technique known as the "coprecipitation method." See, for example, the discussion of preparing magnetite nanoparticles using the coprecipitation method in the article to M. Yamaura et al., "Preparation and characterization of (3-aminopropyl) triethoxysilane-coated magnetite nanoparticles," Journal of Magnetism and Magnetic Materials, Vol. 279, pages 210-217, 2004, which is hereby incorporated herein by reference in its entirety.

An example of a conventional technique of preparing magnetite nanoparticles follows. This conventional example is based on an example set forth in the M. Yamaura et al. article. A 5 mol/l NaOH solution is added into a mixed solution of 0.25 mol/l ferrous chloride and 0.5 mol/l ferric chloride (molar ratio 1:2) until obtaining pH 11 at room temperature. The slurry is washed repeatedly with distilled water. Then, the resulting magnetite nanoparticles are magnetically separated from the supernatant and redispersed in aqueous solution at least three times, until obtaining pH 7. The M. Yamaura et al. article reports that a typical average diameter of the resulting magnetite nanoparticles is 12 nm.

In each of the stages 6(*a*)-6(*f*), the structure is shown in a cross-sectional side view. The method 600 is a modified version of the shell-in-shell microcapsule concept disclosed in Kreft et al., "Shell-in-Shell Microcapsules: A Novel Tool for Integrated, Spatially Confined Enzymatic Reactions", Angewandte Chemie International Edition, Vol. 46, 2007, pp. 5605-5608, which is hereby incorporated herein by reference in its entirety.

The method 600 begins by preparing spherical calcium carbonate microparticles in which finely powdered iron and magnetite nanoparticles are immobilized by coprecipitation (step 605). Optionally, a catalyst such as ferric nitrate may be immobilized in the spherical calcium carbonate microcapsules as well as the iron powder and the magnetite nanoparticles. For example, 1M $CaCl_2$ (0.615 mL), 1M $Na_2CO_3$ (0.615 mL), 1.4% (w/v) magnetite nanoparticle suspension (50 µL) and deionized water (2.450 mL) containing finely powdered iron (2 mg) and, optionally, $Fe(NO_3)_3$ (0.01 mg) may be rapidly mixed and thoroughly agitated on a magnetic stirrer for 20 s at room temperature. After the agitation, the precipitate may be separated from the supernatant by centrifugation and washed three times with water. One of the resulting $CaCO_3$ microparticles is shown at stage 6(*b*).

The diameter of the $CaCO_3$ microparticles produced with a reaction time of 20 s is 4-6 µm. Smaller $CaCO_3$ microparticles are produced if the reaction time is reduced from 20 s to several seconds.

One skilled in the art will appreciate that other metals may be used in lieu of, or in addition to, the iron powder. For example, magnesium or magnesium-iron alloy may also be used.

One skilled in the art will appreciate that other magnetic nanoparticles may be used in lieu of, or in addition to, the magnetite. For example, cobalt ferrite nanoparticles may also be used.

As noted above, the iron powder may be mixed with a catalyst such as ferric nitrate, which when in contact with the hydrogen peroxide (to be encapsulated in the outer shell) liberates oxygen to react exothermically with the iron powder. One skilled in the art will appreciate that other catalysts may be used in lieu of, or in addition to, the ferric nitrate. For example, sodium iodide (NaI) may also be used.

In this example, the fabrication of polyelectrolyte capsules is based on the layer-by-layer (LbL) self-assembly of polyelectrolyte thin films. Such polyelectrolyte capsules are fabricated by the consecutive adsorption of alternating layer of positively and negatively charged polyelectrolytes onto sacrificial colloidal templates. Calcium carbonate is but one example of a sacrificial colloidal template. One skilled in the art will appreciate that other templates may be used in lieu of, or in addition to, calcium carbonate. For example, in accordance with other embodiments of the present disclosure, polyelectrolyte capsules may be templated on melamine formaldehyde and silica.

The method 600 continues by LbL coating the $CaCO_3$ microparticles (step 610). In step 610, a polyelectrolyte multilayer (PEM) build-up may be employed by adsorbing five bilayers of negative PSS (poly(sodium 4-styrenesulfonate); Mw=70 kDa) and positive PAH (poly(allylamine hydrochloride); Mw=70 kDa) (2 mg/mL in 0.5 M NaCl) by using the layer-by-layer assembly protocol. For example, the $CaCO_3$ microparticles produced in step 605 may be dispersed in a 0.5 M NaCl solution with 2 mg/mL PSS (i.e., polyanion) and shaken continuously for 10 min. The excess polyanion may be removed by centrifugation and washing with deionized water. Then, 1 mL of 0.5 M NaCl solution containing 2 mg/mL PAH (i.e., polycation) may be added and shaken continuously for 10 min. The excess polycation may be removed by centrifugation and washing with deionized water. This deposition process of oppositely charged polyelectrolyte may be repeated five times and, consequently, five PSS/PAH bilayers are deposited on the surface of the $CaCO_3$ microparticles. One of the resulting polymer coated $CaCO_3$ microparticles is shown at stage 6(c).

Alternatively, as noted above, in step 610, magnetic nanoparticles may be used in the polyelectrolyte multilayer (PEM) build-up. That is, magnetic nanoparticles may be incorporated into the "inner shell" polyelectrolyte multilayer for the purpose of adapting the inner shell of the shell-in-shell microcapsule to rupture in responsive to a magnetic field. The shell-in-shell microcapsule that results from this optional incorporation of magnetic nanoparticles into the inner shell corresponds to the multi-compartment microcapsule shown in FIG. 3C. For example, the $CaCO_3$ microparticles produced in step 605 may be dispersed in a 0.5 M NaCl solution with $Fe_3O_4$ nanoparticles (citric acid modified, 2 mg/mL) and shaken continuously for 10 min. The excess magnetite nanoparticles may be removed by centrifugation and washing with deionized water. Then, 1 mL of 0.5 M NaCl solution containing 2 mg/mL PAH (polycation) may be added and shaken continuously for 10 min. The excess polycation may be removed by centrifugation and washing with deionized water. This deposition process may be repeated five times and, consequently, five $Fe_3O_4$/PAH bilayers are deposited on the surface of the $CaCO_3$ microparticles.

One skilled in the art will appreciate that other magnetic nanoparticles may be used in lieu of, or in addition to, the $Fe_3O_4$ nanoparticles. For example, cobalt ferrite nanoparticles may also be used.

The thickness of this "inner shell" polyelectrolyte multilayer may be varied by changing the number of bilayers. Generally, it is desirable for the inner shell to rupture while the outer shell remains intact so that the reactants and the reaction products do not contaminate the sealant or adhesive into which the multi-compartment microcapsule may be dispersed. Typically, for a given shell diameter, thinner shells rupture more readily than thicker shells. Hence, in accordance with some embodiments of the present disclosure, the inner shell is made relatively thin compared to the outer shell. On the other hand, the inner shell must not be so thin as to rupture prematurely.

The PSS/PAH-multilayer in step 610, is but one example of a polyelectrolyte multilayer. One skilled in the art will appreciate that other polyelectrolyte multilayers and other coatings may be used in lieu of, or in addition to, the PSS/PAH-multilayer in step 610. For example, coating polyelectrolyte multilayer capsules with lipids can result in a significant reduction of the capsule wall permeability.

The method 600 continues by preparing ball-in-ball calcium carbonate microparticles in which hydrogen peroxide is immobilized by a second coprecipitation (step 615). The ball-in-ball $CaCO_3$ microparticles are characterized by a polyelectrolyte multilayer that is sandwiched between two calcium carbonate compartments. In step 615, the polymer coated $CaCO_3$ microparticles may be resuspended in 1M $CaCl_2$ (0.615 mL), 1M $Na_2CO_3$ (0.615 mL), and deionized water (2.500 mL) containing hydrogen peroxide (1 mg), rapidly mixed and thoroughly agitated on a magnetic stirrer for 20 s at room temperature. After the agitation, the precipitate may be separated from the supernatant by centrifugation and washed three times with water. Unfortunately, the second coprecipitation is accompanied by formation of a coproduct, i.e., single core $CaCO_3$ microparticles that contain only hydrogen peroxide. Hence, the resulting precipitate represents a mixture of ball-in-ball $CaCO_3$ microparticles and single core $CaCO_3$ microparticles. The ball-in-ball $CaCO_3$ microparticles, which are magnetic due to the immobilized magnetite nanoparticles in the inner compartment, may be isolated by applying an external magnetic field to the sample while all of the nonmagnetic single core $CaCO_3$ microparticles are removed by a few washing steps. One of the resulting ball-in-ball $CaCO_3$ microparticles is shown at stage 6(d).

One skilled in the art will appreciate that other oxidizers may be used in lieu of, or in addition to, the hydrogen peroxide. For example, water may also be used.

The method 600 continues by LbL coating the ball-in-ball $CaCO_3$ microparticles (step 620). In step 620, a polyelectrolyte multilayer (PEM) build-up may be employed by adsorbing five bilayers of negative PSS (poly(sodium 4-styrenesulfonate); Mw=70 kDa) and positive PAH (poly(allylamine hydrochloride); Mw=70 kDa) (2 mg/mL in 0.5 M NaCl) by using the layer-by-layer assembly protocol. For example, the ball-in-ball $CaCO_3$ microparticles produced in step 615 may be dispersed in a 0.5 M NaCl solution with 2 mg/mL PSS (i.e., polyanion) and shaken continuously for 10 min. The excess polyanion may be removed by centrifugation and washing with deionized water. Then, 1 mL of 0.5 M NaCl solution containing 2 mg/mL PAH (i.e., polycation) may be added and shaken continuously for 10 min. The excess polycation may be removed by centrifugation and washing with deionized water. This deposition process of oppositely charged polyelectrolyte may be repeated five times and, consequently, five PSS/PAH bilayers are deposited on the surface of the ball-in-ball $CaCO_3$ microparticles. One of the resulting polymer coated ball-in-ball $CaCO_3$ microparticles is shown at stage 6(e).

The thickness of this "outer shell" polyelectrolyte multilayer may be varied by changing the number of bilayers. Generally, it is desirable for the inner shell to rupture while the outer shell remains intact so that the reactants and the reaction products do not contaminate the sealant or adhesive into which the multi-compartment microcapsule is dispersed. Typically, for a given shell diameter, thinner shells rupture more readily than thicker shells. Hence, in accordance with some embodiments of the present disclosure, the outer shell is made relatively thick compared to the inner shell.

The PSS/PAH-multilayer in step 620, is but one example of a polyelectrolyte multilayer. One skilled in the art will appreciate that other polyelectrolyte multilayers and other coatings may be used in lieu of, or in addition to, the PSS/PAH-multilayer in step 620. As noted above, coating polyelectrolyte multilayer capsules with lipids, for example, can result in a significant reduction of the capsule wall permeability.

The method 600 concludes with $CaCO_3$ extraction (step 625). In step 625, the $CaCO_3$ core of the ball-in-ball $CaCO_3$ microparticles may be removed by complexation with ethylenediaminetetraacetic acid (EDTA) (0.2 M, pH 7.5) leading to formation of shell-in-shell microcapsules. For example, the ball-in-ball $CaCO_3$ microparticles produced in step 620 may be dispersed in 10 mL of the EDTA solution (0.2 M, pH 7.5) and shaken for 4 h, followed by centrifugation and re-dispersion in fresh EDTA solution. This core-removing process may be repeated several times to completely remove the $CaCO_3$ core. The size of the resulting shell-in-shell microcapsules ranges from 8-10 μm and the inner core diameter is 3-5 μm. One of the resulting shell-in-shell microcapsules is shown at stage 6(*f*).

As noted above, the fabrication of polyelectrolyte capsules in method 600 is based on the layer-by-layer (LbL) self-assembly of polyelectrolyte thin films. One skilled in the art will appreciate that a multi-compartment microcapsule for heat generation in accordance with some embodiments of the present disclosure may be produced by other conventional multi-compartment systems, such as polymeric micelles, hybrid polymer microspheres, and two-compartment vesicles.

Figure 7:
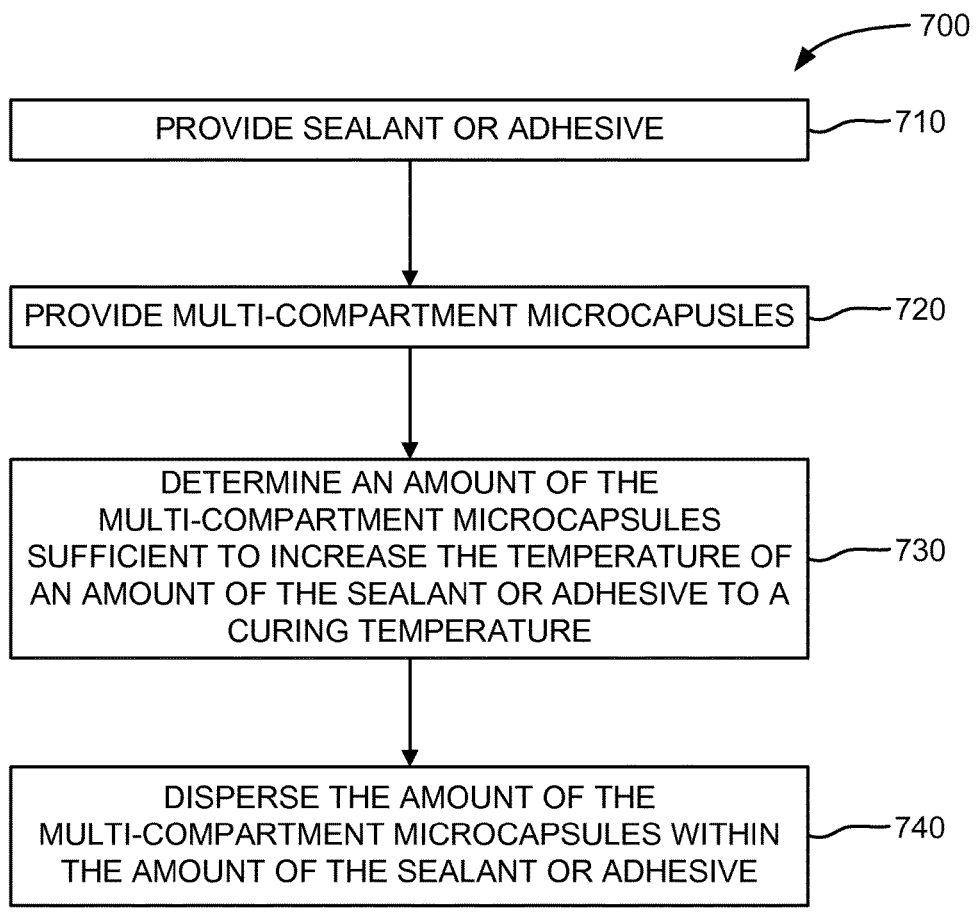
FIG. 7 is a flow diagram illustrating an exemplary method of producing a self-heating sealant or adhesive according to some embodiments of the present disclosure.

FIG. 7 is a flow diagram illustrating an exemplary method 700 of producing a self-heating sealant or adhesive according to some embodiments of the present disclosure. In the method 700, the steps discussed below (steps 710-740) are performed. These steps are set for the in their preferred order. It must be understood, however, that the various steps may occur simultaneously or at other times relative to one another. Moreover, those skilled in the art will appreciate that one or more steps may be omitted.

FIG. 7 exemplifies a method 700 of producing a self-heating sealant or adhesive, particularly in an embodiment using a multi-compartment microcapsule having a shell-in-shell architecture. Various manners of modifying or adapting the method to a variety of embodiments, including other embodiments of a multi-compartment microcapsule to disperse within a sealant or adhesive, will be apparent to one of ordinary skill in the art. The method 700 should be understood to illustrate one manner of producing a self-heating sealant or adhesive for purposes of understanding the disclosure and should not be considered as limiting the embodiments.

The method 700 begins by providing sealant or adhesive (step 710). In step 710, a sealant or adhesive may be chosen with consideration for the application of that sealant or adhesive to a particular substrate or substrates. In one embodiment, a sealant or adhesive may be chosen for application in sealing the periphery of a liquid crystal layer between a TFT array substrate and a color filter substrate and a heat-curable epoxy resin, such as previously disclosed herein, may be selected. In other embodiments, a sealant or adhesive may be chosen for application in sealing or adhering other substrates. For example, a sealant or adhesive may be chosen for an application in adhering and forming electrical connections between the transparent display/backlight electrodes of an LCD module and a driver FPC and an anisotropically conductive adhesive, such as previously disclosed herein, may be selected.

Also in step 710, the curing temperature of the sealant or adhesive may be determined. In addition, a desired thickness, or a desired range of thickness, of a bond line of the sealant or adhesive suitable for the application may be determined in step 710. For example, the desired thickness may be less than 5 microns or may be less than 2 microns. A desired thickness may be determined in relationship to a particular compliance, or range of compliance, values of the sealant or adhesive, and a temperature of the sealant or adhesive that may produce the compliance may be determined.

The method 700 continues by providing multi-compartment microcapsules (step 720). Step 720 may, for example, correspond to the method 600 (shown in FIG. 6) of producing a multi-compartment microcapsule having a shell-in-shell architecture with an inner shell contained within an outer shell, wherein the inner shell is adapted to rupture in response to a compressive force and/or magnetic field according to some embodiments of the present disclosure.

At step 720, exothermic reactants compatible with the materials suitable for forming a microcapsule may be chosen. The exothermic reactants may be chosen to be inert with respect to the selected sealant or adhesive, the material of the microcapsule walls, or an isolating barrier within a microcapsule when the reactants are not in contact. The exothermic reactants also may be chosen to be inert with respect to the sealant or adhesive or the outer microcapsule wall when the reactants are in contact, or such that the chemical products of the reaction are inert with respect to the sealant or adhesive, outer microcapsule wall, and any remnants of the inner microcapsule wall or barrier.

Also at step 720, an amount of the first reactant and an amount of the second reactant may be determined. The amounts may be determined from the total amount of the reactants required to produce a desired amount of heat, the ratio of each reactant according to a reaction equation, the desired dimensions of the microcapsule, and the manner of isolating the reactants within the capsule. For example, a microcapsule may be desired having a maximum dimension less than or equal to a desired final thickness of a sealant or adhesive bond line, such as less than 0.5 microns, and the amount of reactants may be chosen corresponding to the volume available within a microcapsule formed according to that dimension.

In addition, at step 720, one or more inner microcapsules, such as illustrated by microcapsule 302 of FIG. 3A, may be formed and the inner microcapsules may contain a first or a second reactant. In various embodiments, an inner microcapsule may be formed to contain a mixture of fine iron powder and ferric nitrate, or may be formed to contain hydrogen peroxide. The inner microcapsule(s) may be formed with a capsule wall configured to rupture with application of a compressive force. The force required to rupture an inner microcapsule wall may be determined from within the range of compressive force typical of that applied in the manufacture or repair of electronic assemblies (e.g., during the process of assembling liquid crystal cells, during the process of assembling LCD modules, and the like).

Still further, at step 720, an outer microcapsule may be formed containing the inner microcapsule(s) and one or more other reactants, in the manner of multi-compartment microcapsule 300 in FIG. 3A. The reactant(s) contained in the outer microcapsule may be inert with respect to each other and the microcapsule walls until in contact with one or more reactants contained in one or more inner microcapsules. In one embodiment, an outer microcapsule may contain hydrogen peroxide, or other oxidizers, where one or more inner microcapsules contain finely powered iron and ferric nitrate, or other reductants. In another embodiment, the outer microcapsule may contain finely powered iron and ferric nitrate, or other reductants, where one or more inner microcapsules may contain hydrogen peroxide or other oxidizers. The capsule wall of the outer microcapsule may be formed to not rupture at the compressive force applied to rupture the capsule wall of the inner microcapsule.

Alternatively, an embodiment may utilize a microcapsule having a structure as illustrated by multi-compartment microcapsule 310 in FIG. 3B. In accordance with this alternative embodiment, at step 720, an outer microcapsule may be formed having one or more membranes 314, in the manner of multi-compartment microcapsule 310 in FIG. 3B, forming two (or more) compartments within the outer microcapsule. The particular reactants described above may be contained within the compartments, and the membrane(s) may be formed to rupture at compressive forces such as described above with respect to the capsule wall of an inner microcapsule.

In another alternative, an embodiment may utilize a microcapsule having a structure as illustrated by multi-compartment microcapsule 320 in FIG. 3C. In accordance with this alternative embodiment, at step 720, the capsule wall of the inner microcapsule (i.e., the inner shell of the multi-compartment microcapsule 320) may be formed with one or more magnetic nanoparticles so as to rupture under a particular magnetic field through magnetic stimulation of the one or more magnetic nanoparticles and the outer wall of the microcapsule (i.e., the outer shell of the multi-compartment microcapsule 320) may be formed so as to not rupture under that magnetic field. For example, as described above with reference to FIG. 6, for the purpose of adapting the inner shell of the shell-in-shell microcapsule to rupture in responsive to a magnetic field, magnetic nanoparticles may be incorporated into the "inner shell" polyelectrolyte multilayer (i.e., the "Polymer" shown at stage 6(c)). The particular reactants described above may be contained within the compartments.

The method 700 continues by determining an amount of the multi-compartment microcapsules (i.e., the multi-compartment microcapsules provided in step 720) sufficient to increase the temperature of an amount of the sealant or adhesive (i.e., the sealant or adhesive provided in step 710) to a curing temperature (step 730). At step 730, a proportional amount of microcapsules may be determined to mix within the sealant or adhesive. The determination may be made according to the amount of heat required to raise a particular amount of sealant or adhesive from the ambient temperature to the temperature required to cure the sealant or adhesive (and/or produce the desired compliance of the sealant or adhesive), considering also the amount of heat produced by compressing (or otherwise activating) a single microcapsule.

The method 700 then concludes by dispersing the amount of the multi-compartment microcapsules with the amount of the sealant or adhesive (step 740). At step 740, an amount of sealant or adhesive to apply to substrate or substrates to be sealed or adhered may be determined, and a corresponding amount of multi-compartment microcapsules may be mixed into the sealant or adhesive. For example, a sealant or adhesive may cure at 100° C., i.e., a temperature of the sealant or adhesive approximately 75 degrees C. above room ambient temperature. This example, utilizing the reactants and reaction described in reference to FIG. 4A through FIG. 4D, may require at least 0.6 grams of the combined amounts of the reactants dispersed within 30 grams of the sealant or adhesive.

In this example, if we assume 30 g of sealant or adhesive is used for a typical application, and further assume a 2 wt % loading of the multi-compartment microcapsules, this yields 0.6 g of the multi-compartment microcapsules. Also, in this example, to achieve a suitable stoichiometry, 57% of the multi-compartment microcapsules will be loaded with finely divided iron powder; 43% with an oxidizer yielding 0.342 g Fe. This mass of iron particles will liberate 2.518 kJ. As a first approximation, 30 g (0.03 kg) of sealant or adhesive requires 0.03 kJ to raise its temperature 1° C. (1.00 kJ/kg C•0.03 kJ/C). Assuming in this example that the heat capacity of the sealant or adhesive is equivalent to that of epoxy cast resin, the heat of reaction in this example would be sufficient to raise the temperature of the 30 g of sealant or adhesive almost 84° C. (2.518 kJ/0.03 kJ/C=83.9° C.). Depending on the desired temperature boost, the loading level and/or stoichiometry can be adjusted.

Figure 8:
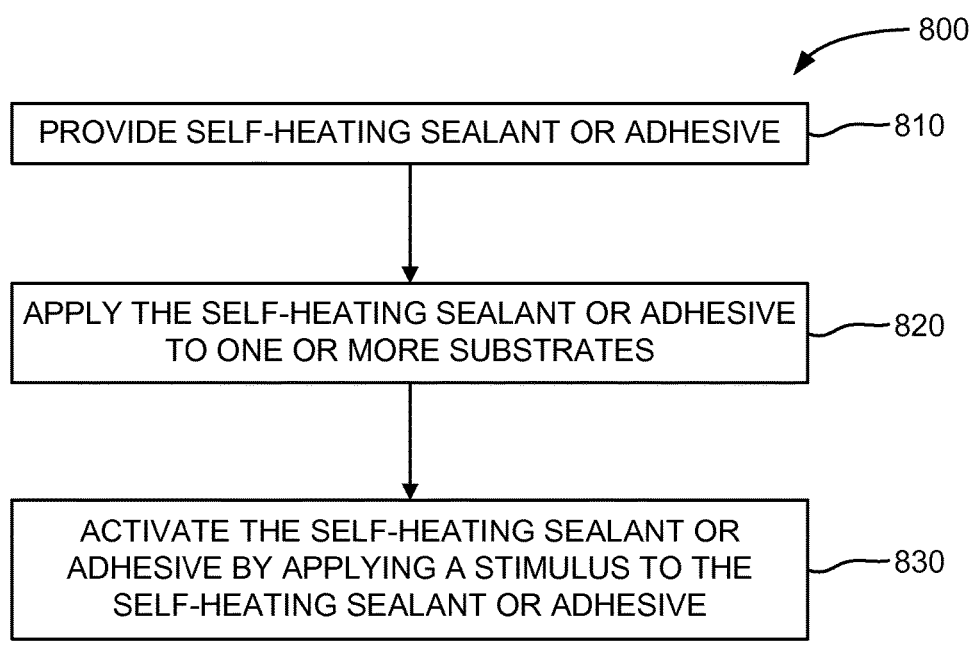
FIG. 8 is a flow diagram illustrating an exemplary method of curing a self-heating sealant or adhesive according to some embodiments of the present disclosure.

FIG. 8 is a flow diagram illustrating an exemplary method 800 of curing a self-heating sealant or adhesive according to some embodiments of the present disclosure. In the method 800, the steps discussed below (steps 810-830) are performed. These steps are set for the in their preferred order. It must be understood, however, that the various steps may occur simultaneously or at other times relative to one another. Moreover, those skilled in the art will appreciate that one or more steps may be omitted.

The method 800 begins by providing a self-heating sealant or adhesive (step 810). Step 810 may, for example, correspond to the method 700 (shown in FIG. 7) of producing a self-heating sealant or adhesive according to some embodiments of the present disclosure.

In step 810, a self-heating TIM may be selected. The selection may consider particular properties of the sealant or adhesive and the substrate or substrates to be sealed or adhered. The particular properties considered may include the thermal and/or electrical conductivity of the sealant or adhesive, the durability of the sealant or adhesive, the shear strength of the sealant or adhesive, the chemical or physical suitability of the sealant or adhesive with the substrate or substrates to be sealed or adhered, the compliance of the sealant or adhesive at the ambient temperature, or the initial and desired final thickness of the sealant or adhesive bond line between the substrates. Other considerations may apply to a particular assembly, devices, manufacturing process, or field repair process and will be evident to one of ordinary skill in the art.

The method 800 continues by applying the self-heating sealant or adhesive to the substrate or substrates to be sealed or adhered (step 820). At step 820, a selected self-heating sealant or adhesive may be applied in the initial bond line thickness.

Also at step 820, an amount of the sealant or adhesive may be determined that produces an initial bond line thickness between the substrates to be sealed or adhered. The compliance of the sealant or adhesive at the ambient temperature of manufacture or repair may determine the initial thickness of the sealant or adhesive. For example, in an embodiment, an initial thickness of a sealant or adhesive may be 5.0 microns or more, and a final thickness of the bond line after heating the sealant or adhesive may be desired to be less than 2.0 microns The method 800 then concludes by activating the self-heating sealant or adhesive by applying a stimulus (e.g., a compressive force, a magnetic field, ultrasound, or a combination thereof) to the self-heating sealant or adhesive (step 830). In some embodiments, at step 820, the substrates may be joined together at the bond line of the sealant or adhesive and joining the substrates may compress the sealant or adhesive. In other embodiments, at step 820, the substrates may be pressed together to compress the sealant or adhesive, until the sealant or adhesive may cure, at the bond line of the sealant or adhesive. Accordingly, the compressive force applied to the sealant or adhesive may vary within a range typical of the manufacture of electronic or mechanical assemblies, or within a range of mechanical pressure applied to join the substrates until the sealant or adhesive has cured or otherwise had effect to seal or adhere the substrates.

Also at step 820, compressing the self-heating sealant or adhesive may produce an exothermic reaction acting to heat the sealant or adhesive, and the increased temperature of the sealant may produce a second compliance of the sealant or adhesive, and the second compliance of the sealant or adhesive may produce a desired final thickness of the sealant or adhesive bond line.

In addition, at step 820, the sealant or adhesive and the substrates may be cooled to ambient temperature or to a temperature corresponding to normal operation.

Figure 9:
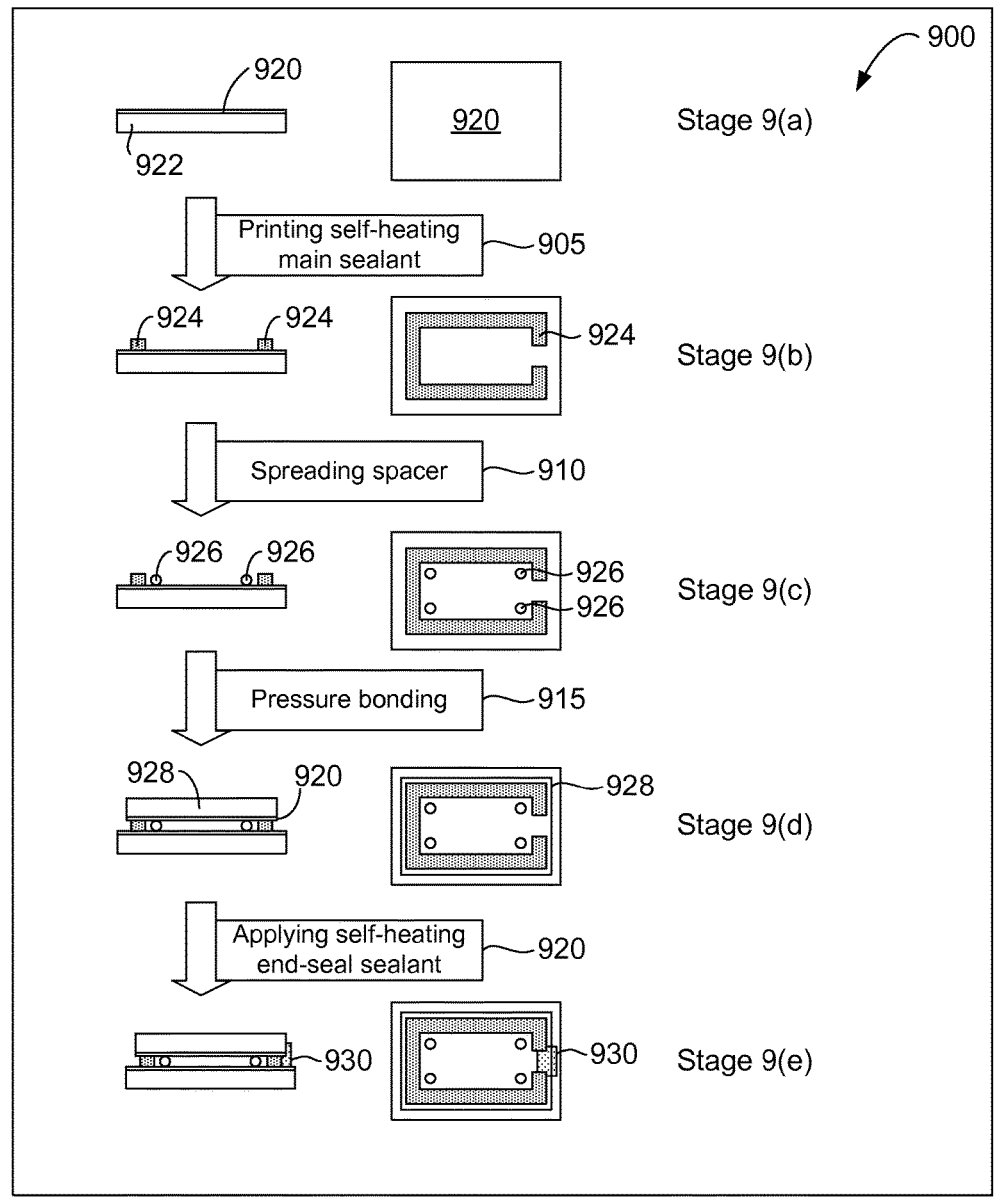
FIG. 9 is a flow diagram illustrating, through stages 9(a)-9(e), a method of assembling liquid crystal cells during TFT LCD panel fabrication, in which a self-heating sealant is used to seal the periphery of a liquid crystal layer between a TFT array substrate and a color filter substrate according to some embodiments of the present disclosure.

FIG. 9 is a flow diagram illustrating, through stages 9(*a*)-9(*e*), a method 900 of assembling liquid crystal cells during thin-film transistor (TFT) liquid crystal display (LCD) panel fabrication, in which a self-heating sealant is used to seal the periphery of a liquid crystal layer between a TFT array substrate and a color filter substrate according to some embodiments of the present disclosure. In the method 900, the steps discussed below (steps 905-920) are performed. These steps are set for the in their preferred order. It must be understood, however, that the various steps may occur simultaneously or at other times relative to one another. Moreover, those skilled in the art will appreciate that one or more steps may be omitted.

In each of the stages 9(*a*)-9(*e*), the structure is shown in a cross-sectional side view and a top view.

Stage 9(*a*). As is conventional, the method 900 of assembling liquid crystal cells begins by printing a polyimide alignment film 920 on both a TFT array substrate 922 and a color filter substrate (928 shown in stage 9(*d*)). These substrates are typically sized so that multiple (e.g., six, eight, nine, or twelve) cells can be produced simultaneously. Only one cell is shown in FIG. 9 for the sake of clarity. The surface of each polyimide alignment film is then rubbed (e.g., with a piece of cloth wound on a roller) to orient the polyimide molecules in one direction.

Stage 9(*b*). After completing the rubbing process, a self-heating sealant 924 is applied to the periphery of the TFT array substrate 920 (step 905). The self-heating sealant 924 corresponds with the LCD panel main sealant 102 shown in FIGS. 1 and 2. The self-heating sealant 924 may be, for example, a heat-curable epoxy resin in which the multi-compartment microcapsules are dispersed. Alternatively, the self-heating sealant may be, for example, a UV+heat-curable epoxy resin, such as LOCTITE ECCOBOND DS 6601, in which the multi-compartment microcapsules are dispersed. In addition, the TFT array substrate 920 may be coated with a conducting paste (not shown) around its periphery to form electrical connections between electrodes on the color filter substrate and electrodes on the TFT array substrate. Alternatively, the self-heating sealant 924 may be applied to the periphery of the color filter substrate.

Stage 9(*c*). The method 900 continues by spreading one or more spacers (step 910). Spacers control the cell gap and are sprayed onto the TFT array substrate 922. Alternatively, the spacers may be sprayed onto the color filter substrate 928.

Stage 9(*d*). The TFT array substrate 922 and the color filter substrate 928 are brought together, aligned, and subjected to pressure bonding to activate the self-heating sealant 924 (step 915). For example, a conventional UV press (typically utilized to cure conventional UV-curing resins) or a conventional hot press (typically utilized to cure heat-curing resins) may be employed to exert a compressive force on the self-heating sealant 924 sufficient to rupture the isolating structures of the multi-compartment microcapsules. If the self-heating sealant 924 is a heat-curable epoxy resin in which the multi-compartment microcapsules are dispersed, the multi-compartment microcapsules may generate the heat necessary for heat-curing. If the self-heating sealant 924 is a UV+heat-curable epoxy resin in which the multi-compartment microcapsules are dispersed, the multi-compartment microcapsules may generate the heat necessary for post cure (i.e., subsequent to UV-curing). The substrate assembly may then be scribed (e.g., using a diamond wheel) and separated into individual cells (each cell corresponds to a TFT LCD panel). Once separated, the empty cells are filled with liquid crystal material by vacuum injection.

Stage 9(*e*). An end-seal sealant 930 is then used to seal the cell (step 920). The end-seal sealant 930 may be a self-heating sealant. The end-seal sealant 930 corresponds with the LCD panel end sealant 104 shown in FIGS. 1 and 2. The end-seal sealant 930 may be, for example, a heat-curable epoxy resin in which the multi-compartment microcapsules are dispersed. If the end-seal sealant 930 is a heat-curable epoxy resin in which the multi-compartment microcapsules are dispersed, the multi-compartment microcapsules may generate the heat necessary for heat-curing. Alternatively, the end-seal sealant 930 may be, for example, a UV+heat-curable epoxy resin, such as LOCTITE ECCOBOND DS 6601, in which the multi-compartment microcapsules are dispersed. If the end-seal sealant 930 is a UV+heat-curable epoxy resin in which the multi-compartment microcapsules are dispersed, the multi-compartment microcapsules may generate the heat necessary for post cure (i.e., subsequent to UV-curing). The multi-compartment microcapsules contained in the end-seal sealant 930 may be activated, for example, by a compressive force applied by a sealant dispenser (e.g., a dispensing head used to dispense the end-seal sealant 930).

One skilled in the art will appreciate that many variations are possible within the scope of the present invention. Thus, while the present invention has been particularly shown and described with reference to particular embodiments thereof, it will be understood by those skilled in the art that these and other changes in form and detail may be made therein without departing from the spirit and scope of the present invention.

What is claimed is:

1. A method of producing a self-heating sealant or adhesive, the method comprising:
   providing a sealant or adhesive;
   providing multi-compartment microcapsules each having a first compartment and a second compartment separated from each other by an isolating structure adapted to rupture in response to a stimulus, wherein the first and second compartments of each multi-compartment microcapsule contain reactants that come in contact and react to produce heat when the isolating structure ruptures;

adding the multi-compartment microcapsules to the sealant or adhesive.

2. The method as recited in claim 1, wherein the stimulus is selected from a group consisting of a compressive force, a magnetic field, and combinations thereof.

3. The method as recited in claim 1, wherein the sealant is selected from the group consisting of an epoxy-based sealant, an acrylic-based sealant, a silicone-based sealant, and combinations thereof.

4. The method as recited in claim 1, wherein the adhesive is selected from the group consisting of an epoxy-based adhesive, an acrylic-based adhesive, a silicone-based adhesive, and combinations thereof.

5. The method as recited in claim 1, further comprising determining an amount of the multi-compartment microcapsules sufficient to increase the temperature of an amount of the sealant or adhesive from a first temperature to a curing temperature, and wherein adding the multi-compartment microcapsules to the sealant or adhesive includes dispersing the amount of the multi-compartment microcapsules within the amount of the sealant or adhesive.

6. The method as recited in claim 1, wherein the first compartment contains a metal and the second compartment contains an oxidizer.

7. The method as recited in claim 1, wherein the multi-compartment microcapsules are shell-in-shell microcapsules each comprising an inner shell contained within an outer shell, wherein the inner shell encapsulates the first compartment, wherein the outer shell encapsulates the second compartment, and wherein the inner shell defines the isolating structure.

8. The method as recited in claim 7, wherein the first compartment contains iron, and wherein the second compartment contains hydrogen peroxide.

9. The method as recited in claim 7, wherein the first compartment contains iron and ferric nitrate, and wherein the second compartment contains hydrogen peroxide.

10. A method of producing a self-heating sealant, the method comprising:

providing a sealant;

providing multi-compartment microcapsules each having a first compartment and a second compartment separated from each other by an isolating structure adapted to rupture in response to a stimulus, wherein the first and second compartments of each multi-compartment microcapsule contain reactants that come in contact and react to produce heat when the isolating structure ruptures;

adding the multi-compartment microcapsules to the sealant.

11. A method of producing a self-heating adhesive, the method comprising:

providing an adhesive;

providing multi-compartment microcapsules each having a first compartment and a second compartment separated from each other by an isolating structure adapted to rupture in response to a stimulus, wherein the first and second compartments of each multi-compartment microcapsule contain reactants that come in contact and react to produce heat when the isolating structure ruptures;

adding the multi-compartment microcapsules to the adhesive.

* * * * *